United States Patent
Folan

(10) Patent No.: US 12,064,333 B2
(45) Date of Patent: *Aug. 20, 2024

(54) STENT WITH ATRAUMATIC SPACER

(71) Applicant: BOSTON SCIENTIFIC SCIMED, INC., Maple Grove, MN (US)

(72) Inventor: Martyn G. Folan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/707,318

(22) Filed: Mar. 29, 2022

(65) Prior Publication Data
US 2022/0218461 A1 Jul. 14, 2022

Related U.S. Application Data

(63) Continuation of application No. 16/169,370, filed on Oct. 24, 2018, now Pat. No. 11,304,795.
(Continued)

(51) Int. Cl.
*A61F 2/07* (2013.01)
*A61F 2/86* (2013.01)
(Continued)

(52) U.S. Cl.
CPC .............. *A61F 2/07* (2013.01); *A61F 2/86* (2013.01); *A61F 2/90* (2013.01); *A61F 2/04* (2013.01);
(Continued)

(58) Field of Classification Search
CPC ........ A61F 2/07; A61F 2/86; A61F 2002/041; A61F 2230/0008; A61F 2250/0018;
(Continued)

(56) References Cited

U.S. PATENT DOCUMENTS 5,064,435 A 11/1991 Porter
5,474,563 A 12/1995 Myler et al.
(Continued)

FOREIGN PATENT DOCUMENTS

EP 1065996 B1 12/2003
EP 1229864 B1 4/2005
(Continued)

OTHER PUBLICATIONS

"Axios Stent and Electrocautery Enhanced Delivery System," Boston Scientific, 4 pages, Dec. 2015.
(Continued)

*Primary Examiner* — Paul B Prebilic
(74) *Attorney, Agent, or Firm* — Seager, Tufte & Wickhem, LLP

(57) ABSTRACT

A stent includes a tubular body formed of one or more interwoven wires, the tubular body having first and second opposing open ends and a lumen extending therebetween. The stent further includes a first anchor member disposed adjacent the first open end and a second anchor member disposed adjacent the second open end, the first and second anchor members each extending radially outward from the tubular body, the first and second anchor members each having an outer diameter larger than an outer diameter of the tubular body disposed between the first and second anchor members. A plurality of spacer members are disposed around the first open end and extending longitudinally beyond the first open end, wherein when a pulling force is applied to the spacer members, the outer diameter of the tubular body is not reduced.

17 Claims, 10 Drawing Sheets

Related U.S. Application Data

(60) Provisional application No. 62/576,890, filed on Oct. 25, 2017.

(51) Int. Cl.
  *A61F 2/90* (2013.01)
  *A61F 2/04* (2013.01)

(52) U.S. Cl.
  CPC ... *A61F 2002/041* (2013.01); *A61F 2002/043* (2013.01); *A61F 2002/044* (2013.01); *A61F 2002/046* (2013.01); *A61F 2230/0008* (2013.01); *A61F 2250/0018* (2013.01); *A61F 2250/0036* (2013.01); *A61F 2250/0039* (2013.01); *A61F 2250/0098* (2013.01)

(58) Field of Classification Search
  CPC ...... A61F 2250/0036; A61F 2250/0039; A61F 2250/0098
  See application file for complete search history.

(56) References Cited

U.S. PATENT DOCUMENTS

| | | | |
|---|---|---|---|
| 5,632,772 A * | 5/1997 | Alcime | A61F 2/07 623/1.35 |
| 5,741,333 A | 4/1998 | Frid | |
| 5,849,037 A | 12/1998 | Frid | |
| 5,888,201 A | 3/1999 | Stinson et al. | |
| 5,941,895 A | 8/1999 | Myler et al. | |
| 5,980,533 A | 11/1999 | Holman | |
| 6,120,522 A | 9/2000 | Vrba et al. | |
| 6,240,978 B1 | 6/2001 | Gianotti | |
| 6,241,757 B1 | 6/2001 | An et al. | |
| 6,264,689 B1 | 7/2001 | Colgan et al. | |
| 6,290,721 B1 | 9/2001 | Heath | |
| 6,295,714 B1 | 10/2001 | Roychowdhury et al. | |
| 6,302,917 B1 | 10/2001 | Dua et al. | |
| 6,423,084 B1 | 7/2002 | St. Germain | |
| 6,468,303 B1 | 10/2002 | Amplatz et al. | |
| 6,558,429 B2 | 5/2003 | Taylor | |
| 6,569,181 B1 | 5/2003 | Burns | |
| 6,585,758 B1 | 7/2003 | Chouinard et al. | |
| 6,620,122 B2 | 9/2003 | Stinson et al. | |
| 6,626,936 B2 | 9/2003 | Stinson | |
| 6,626,939 B1 | 9/2003 | Burnside et al. | |
| 6,652,577 B2 | 11/2003 | Gianotti | |
| 6,663,663 B2 | 12/2003 | Kim et al. | |
| 6,792,979 B2 | 9/2004 | Konya et al. | |
| 6,821,291 B2 | 11/2004 | Bolea et al. | |
| 6,997,945 B2 | 2/2006 | St. Germain | |
| 7,001,423 B2 | 2/2006 | Euteneuer et al. | |
| 7,001,425 B2 | 2/2006 | McCullagh et al. | |
| 7,018,401 B1 | 3/2006 | Hyodoh et al. | |
| 7,048,014 B2 | 5/2006 | Hyodoh et al. | |
| 7,101,392 B2 | 9/2006 | Heath | |
| 7,160,323 B2 | 1/2007 | Pulnev et al. | |
| 7,172,617 B2 | 2/2007 | Colgan et al. | |
| 7,175,655 B1 | 2/2007 | Molaei | |
| 7,311,031 B2 | 12/2007 | McCullagh et al. | |
| 7,331,990 B2 | 2/2008 | Gianotti | |
| 7,419,502 B2 | 9/2008 | Pulnev et al. | |
| 7,419,503 B2 | 9/2008 | Pulnev et al. | |
| 7,462,192 B2 | 12/2008 | Norton et al. | |
| 7,476,256 B2 | 1/2009 | Meade et al. | |
| 7,637,938 B2 | 12/2009 | Brown et al. | |
| 7,655,039 B2 | 2/2010 | Leanna et al. | |
| 7,670,367 B1 | 3/2010 | Chouinard et al. | |
| 7,670,369 B2 | 3/2010 | Schaeffer | |
| 7,736,386 B2 | 6/2010 | Pulnev et al. | |
| 7,763,011 B2 | 7/2010 | Ortiz et al. | |
| 7,763,068 B2 | 7/2010 | Pulnev et al. | |
| 7,815,591 B2 | 10/2010 | Levine et al. | |
| 7,857,844 B2 | 12/2010 | Norton et al. | |
| 7,927,366 B2 | 4/2011 | Pulnev et al. | |
| 8,092,512 B2 | 1/2012 | Rudnick et al. | |
| 8,105,392 B2 | 1/2012 | Durgin | |
| 8,109,992 B2 | 2/2012 | Pulnev et al. | |
| 8,114,147 B2 | 2/2012 | Wood et al. | |
| 8,151,682 B2 | 4/2012 | Lilburn et al. | |
| 8,197,528 B2 | 6/2012 | Colgan et al. | |
| 8,197,529 B2 | 6/2012 | Cully et al. | |
| 8,211,186 B2 | 7/2012 | Belhe et al. | |
| 8,262,719 B2 | 9/2012 | Erickson et al. | |
| 8,357,193 B2 | 1/2013 | Phan et al. | |
| 8,414,635 B2 | 4/2013 | Hyodoh et al. | |
| 8,425,539 B2 | 4/2013 | Binmoeller et al. | |
| 8,454,632 B2 | 6/2013 | Binmoeller et al. | |
| 8,459,164 B2 | 6/2013 | Lilburn et al. | |
| 8,491,647 B2 | 7/2013 | Colgan et al. | |
| 8,623,071 B2 | 1/2014 | Lundkvist et al. | |
| 8,647,381 B2 | 2/2014 | Essinger et al. | |
| 8,677,874 B2 | 3/2014 | Lilburn et al. | |
| 8,784,473 B2 | 7/2014 | Tupil et al. | |
| 8,926,686 B2 | 1/2015 | King | |
| 9,044,300 B2 | 6/2015 | Belhe et al. | |
| 9,265,634 B2 | 2/2016 | Brady et al. | |
| 9,439,791 B2 | 9/2016 | Vong et al. | |
| 9,526,648 B2 | 12/2016 | Sharma | |
| 9,566,182 B2 | 2/2017 | Durgin | |
| 10,076,330 B2 | 9/2018 | Sander et al. | |
| 2003/0032967 A1 | 2/2003 | Park et al. | |
| 2003/0083734 A1 | 5/2003 | Friedrich et al. | |
| 2004/0093058 A1 | 5/2004 | Cottone et al. | |
| 2005/0049682 A1 | 3/2005 | Leanna et al. | |
| 2006/0190075 A1 | 8/2006 | Jordan et al. | |
| 2006/0276887 A1 | 12/2006 | Brady et al. | |
| 2007/0112415 A1 | 5/2007 | Bartlett | |
| 2007/0112437 A1 | 5/2007 | Shank | |
| 2007/0179590 A1 | 8/2007 | Lu et al. | |
| 2007/0281379 A1 | 12/2007 | Stark et al. | |
| 2008/0243151 A1 | 10/2008 | Binmoeller et al. | |
| 2009/0177268 A1 | 7/2009 | Lundkvist et al. | |
| 2009/0248171 A1 | 10/2009 | Levine et al. | |
| 2009/0281379 A1 | 11/2009 | Binmoeller et al. | |
| 2010/0106240 A1 | 4/2010 | Duggal et al. | |
| 2010/0305590 A1 | 12/2010 | Holmes et al. | |
| 2011/0060398 A1 | 3/2011 | Tupil et al. | |
| 2011/0071613 A1 | 3/2011 | Wood et al. | |
| 2011/0190662 A1 | 8/2011 | McWeeney | |
| 2011/0190905 A1 | 8/2011 | Behan | |
| 2012/0095543 A1 | 4/2012 | Pal | |
| 2012/0259404 A1 * | 10/2012 | Tieu | A61F 2/88 623/1.15 |
| 2013/0030351 A1 | 1/2013 | Belhe et al. | |
| 2013/0053950 A1 | 2/2013 | Rowe et al. | |
| 2013/0144372 A1 | 6/2013 | Wood et al. | |
| 2013/0197623 A1 | 8/2013 | McHugo | |
| 2013/0245745 A1 | 9/2013 | Vong et al. | |
| 2013/0253546 A1 | 9/2013 | Sander et al. | |
| 2014/0074219 A1 | 3/2014 | Hingston et al. | |
| 2014/0074220 A1 | 3/2014 | Clerc et al. | |
| 2014/0081382 A1 | 3/2014 | Leanna et al. | |
| 2014/0081416 A1 | 3/2014 | Clerc et al. | |
| 2014/0156023 A1 | 6/2014 | Blackmon | |
| 2014/0243992 A1 | 8/2014 | Walsh et al. | |
| 2014/0350694 A1 | 11/2014 | Behan | |
| 2014/0364959 A1 | 12/2014 | Attar et al. | |
| 2015/0134074 A1 | 5/2015 | Walsh et al. | |
| 2015/0282922 A1 | 10/2015 | Hingston et al. | |
| 2015/0290005 A1 | 10/2015 | Wainwright et al. | |
| 2015/0342770 A1 | 12/2015 | Howard et al. | |
| 2016/0081832 A1 | 3/2016 | Hingston et al. | |
| 2016/0256257 A1 | 9/2016 | Rasmussen et al. | |
| 2017/0079812 A1 | 3/2017 | Lam et al. | |
| 2017/0333230 A1 * | 11/2017 | Folan | A61F 2/90 |
| 2018/0125633 A1 | 5/2018 | Fikfak et al. | |
| 2018/0263797 A1 | 9/2018 | Eller et al. | |

(56) References Cited

U.S. PATENT DOCUMENTS

2018/0280166 A1 10/2018 Walsh et al.
2020/0261205 A1 8/2020 Folan et al.

FOREIGN PATENT DOCUMENTS

| | | | |
|---|---|---|---|
| EP | 1001718 | B1 | 9/2005 |
| EP | 975279 | B1 | 2/2007 |
| EP | 1560544 | B1 | 1/2008 |
| EP | 2194887 | A2 | 6/2010 |
| EP | 2273942 | A1 | 1/2011 |
| EP | 2276390 | A1 | 1/2011 |
| EP | 1598032 | B1 | 3/2011 |
| EP | 1755462 | B1 | 3/2011 |
| EP | 2389877 | A2 | 11/2011 |
| EP | 2391752 | A2 | 12/2011 |
| EP | 1833417 | B1 | 2/2012 |
| EP | 2407127 | B1 | 4/2014 |
| EP | 2434961 | B1 | 1/2015 |
| JP | 2005211292 | A | 8/2005 |
| JP | 2007517603 | A | 7/2007 |
| JP | 2011509124 | A | 3/2011 |
| JP | 2013504375 | A | 2/2013 |
| JP | 2016519588 | A | 7/2016 |
| JP | 2017510410 | A | 4/2017 |
| WO | 2008103572 | A1 | 8/2008 |
| WO | 2012087301 | A1 | 6/2012 |
| WO | 2016134148 | A1 | 8/2016 |
| WO | 2017015345 | A1 | 1/2017 |

OTHER PUBLICATIONS

Blackwell, What is the mean Lower Esophageal Sphincter Pressure in normal subjects?, Oleso Knowledge, 2 bages, May 1991.

Booth, "Vomiting Larry: a simulated vomiting system for assessing environmental contamination from projectile vomiting related to norovirus infection," Journal of Infection Prevention, 15(5): 8 pages, Sep. 2014.

Bowen, "Phisiology of Vomiting," VIVO Pathophysiology, 4 pages, accessed Aug. 11, 2017.

Cowgill et al., "Normal lower esophageal sphincter pressure and length does not impact outcome after laparoscopic Nissen fundoplication," PubMed, 11(6): 2 pages, Jun. 2007.

Dua et al., "Self-expanding metal esophageal stent with anti-reflux mechanism," Gastrointestinal Endoscopy, 53(6): 2 pages, May 2001.

"Gastroesophageal Reflux Disease," National Cancer Institute, 2 pages, accessed Aug. 11, 2017.

Hayden et al., "Fecal Incontinence: Etiology, Evaluation, and Treatment," Clinics in Colon and Rectal Surgery, 24(1): 9 pages, Mar. 2011.

Mashimo et al., "Physiology of esophageal motility," GI Motility online, 36 pages, May 16, 2006.

"Polyimide Tubing: Dispelling the Myths," MicroLumen High Performance Medical Tubing, 8 pages, 2008.

Sajadi et al., "Artificial Urinary Sphincter Placement Treatment and Management," Medscape, 1 page, May 16, 2016.

Mukai et al; "Interventional Endoscopy for the Treatment of Pancreatic Psudocyst and Walled-Off Necrosis," Journal of Hepato-Biliary-Pancreatic Sciences, 21:E75-E85, 2014.

International Search Report and Written Opinion dated Jan. 22, 2019 for international Application No. PCT/US2018/057308.

Siddiqui et al., "EUS-guided drainage of peripancreatic fluid collections and necrosis by using a novel lumen-apposing stent: a large retrospective, multicenter U.S. experience," Gastrointestinal Endoscopy Journal, 83(4): 9 pages, Apr. 1, 2016.

Lang et al., "EUS-guided drainage of peripancreatic fluid collections with lumen-apposing metal stents and plastic double-pigtail stents: comparison of efficacy and adverse event rates," Gastrointestinal Endoscopy Journal, 29 pages, Jul. 13, 2017.

Siddiqui et al., "Fully covered self-expanding metal stents versus lumen-apposing fully covered self-expanding metal stent versus plastic stents for endoscopic drainage of pancreatic walled-off necrosis: clinical outcomes and success," Gastrointestinal Endoscopy Journal, 85(4): 8 pages, Apr. 2017. (Epub date of Aug. 24, 2016).

* cited by examiner

STENT WITH ATRAUMATIC SPACER

CROSS-REFERENCE TO RELATED APPLICATIONS

This application is a continuation of U.S. patent application Ser. No. 16/169,370, filed Oct. 24, 2018, now U.S. Pat. No. 11,304,795 which claims priority to U.S. Provisional Application Ser. No. 62/576,890, filed Oct. 25, 2017, the entirety of which is incorporated herein by reference.

TECHNICAL FIELD

The present invention relates to devices, methods and systems for implanting stents. More particularly, the present invention relates to implantable stents having atraumatic spacer members.

BACKGROUND

An intraluminal prosthesis is a medical device used in the treatment of bodily lumens. One type of intraluminal prosthesis used in the repair and/or treatment of diseases in various body vessels is a stent. A stent is a generally longitudinal tubular device formed of biocompatible material which is useful to open and support various lumens in the body. For example, stents may be used in the vascular system, urogenital tract, gastrointestinal tract, esophageal tract, tracheal/bronchial tubes and bile duct, as well as in a variety of other applications in the body.

Lumen apposing metal stents are also used to drain pancreatic fluid collections and to provide direct biliary and gallbladder drainage. The positioning of the metal stent adjacent a cyst wall may result in post acute bleeding as the distal surface of the stent and the cyst wall come in contact as the cyst volume reduces due to drainage. Repetitive interaction between the end of the stent, such as a multi-terminal pointed stent end, with the cyst wall may be involved. Accordingly, there is an ongoing need to mitigate or remove this tissue interaction and negate the bleeding when an intraluminal prosthesis, such as a stent, is used for drainage.

SUMMARY

The present disclosure is directed to various embodiments of a stent, for example a braided stent, having an integral spacer mechanism.

A first example stent includes a tubular body formed of one or more interwoven wires, the tubular body having first and second opposing open ends and a lumen extending therebetween, the tubular body defining a longitudinal axis extending between the first and second open ends, a first anchor member disposed adjacent the first open end and a second anchor member disposed adjacent the second open end, the first and second anchor members each extending radially outward from the tubular body, the first and second anchor members each having an outer diameter larger than an outer diameter of the tubular body disposed between the first and second anchor members, and a plurality of spacer members disposed around the first open end and extending longitudinally beyond the first open end, wherein when a pulling force is applied to the spacer members, the outer diameter of the tubular body is not reduced.

Alternatively or additionally to any of the above examples, each spacer member has first and second legs extending along a portion of the tubular body toward the second open end.

Alternatively or additionally to any of the above examples, the spacer members extend radially outward beyond the outer diameter of the tubular body.

Alternatively or additionally to any of the above examples, each spacer member is formed from a single wire loop.

Alternatively or additionally to any of the above examples, the spacer members are formed separately from the tubular body and attached to an inner wall of the tubular body.

Alternatively or additionally to any of the above examples, the spacer members are interwoven with the tubular body.

Alternatively or additionally to any of the above examples, the spacer members are less flexible than the tubular body.

Alternatively or additionally to any of the above examples, the plurality of spacer members includes a first group of spacer members with a first length and a second group of spacer members having a second length shorter than the first length.

Alternatively or additionally to any of the above examples, the first group of spacer members are more flexible than the second group of spacer members.

Alternatively or additionally to any of the above examples, the stent may further include a covering extending over an entirety of the tubular body, first and second anchor members, and the plurality of spacer members.

Alternatively or additionally to any of the above examples, at least one spacer member has a variable flexibility along its length.

Alternatively or additionally to any of the above examples, the at least one spacer member is formed from a tapered wire having a first thickness in a first region adjacent the tubular body, and a second thickness in a second region disposed furthest away from the tubular body.

Alternatively or additionally to any of the above examples, the second thickness is smaller than the first thickness, resulting in a greater flexibility in the second region.

Alternatively or additionally to any of the above examples, the first and second anchor members extend perpendicular to the longitudinal axis.

Alternatively or additionally to any of the above examples, the stent may further include a retrieval element disposed at the second open end.

Another example stent includes a tubular body formed of one or more interwoven wires, the tubular body having first and second opposing open ends and a lumen extending therebetween, the tubular body defining a longitudinal axis extending between the first and second open ends, a first group of spacer members disposed around the first open end and extending longitudinally beyond the first open end and extending radially outward beyond an outer diameter of the tubular body, the first group of spacer members having a first length, a second group of spacer members disposed around the first open end and extending longitudinally beyond the first open end and extending radially outward beyond an outer diameter of the tubular body, the second group of spacer members having a second length shorter than the first length, and wherein when a pulling force is applied to the first and/or second group of spacer members, the outer diameter of the tubular body is not reduced.

Alternatively or additionally to any of the above examples, a first anchor member disposed adjacent the first open end and a second anchor member disposed adjacent the second open end, the first and second anchor members each extending radially outward from the tubular body, the first and second anchor members each having an outer diameter larger than the outer diameter of the tubular body disposed between the first and second anchor members.

Alternatively or additionally to any of the above examples, the first group of spacer members are more flexible than the second group of spacer members.

Alternatively or additionally to any of the above examples, at least one spacer member in the first or second group of spacer members is formed from a tapered wire having a first thickness in a first region adjacent the tubular body, and a second thickness in a second region disposed furthest away from the tubular body, wherein the second thickness is smaller than the first thickness, resulting in a greater flexibility in the second region.

Another example is a method of draining a cyst comprising implanting a stent through a tissue wall with a first open end of the stent disposed within the cyst and a second open end of the stent disposed outside the cyst, the stent including a tubular body formed of one or more interwoven wires, the tubular body defining a lumen extending between the first and second open ends, the stent including a plurality of spacer members disposed around the first open end and extending longitudinally beyond the first open end, and draining fluid from the cyst through the lumen of the stent, wherein as the cyst drains, a wall of the cyst comes into contact with one or more of the plurality of spacer members, wherein the plurality of spacer members prevents the wall of the cyst from contacting the first open end of the stent.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

Figure 1:
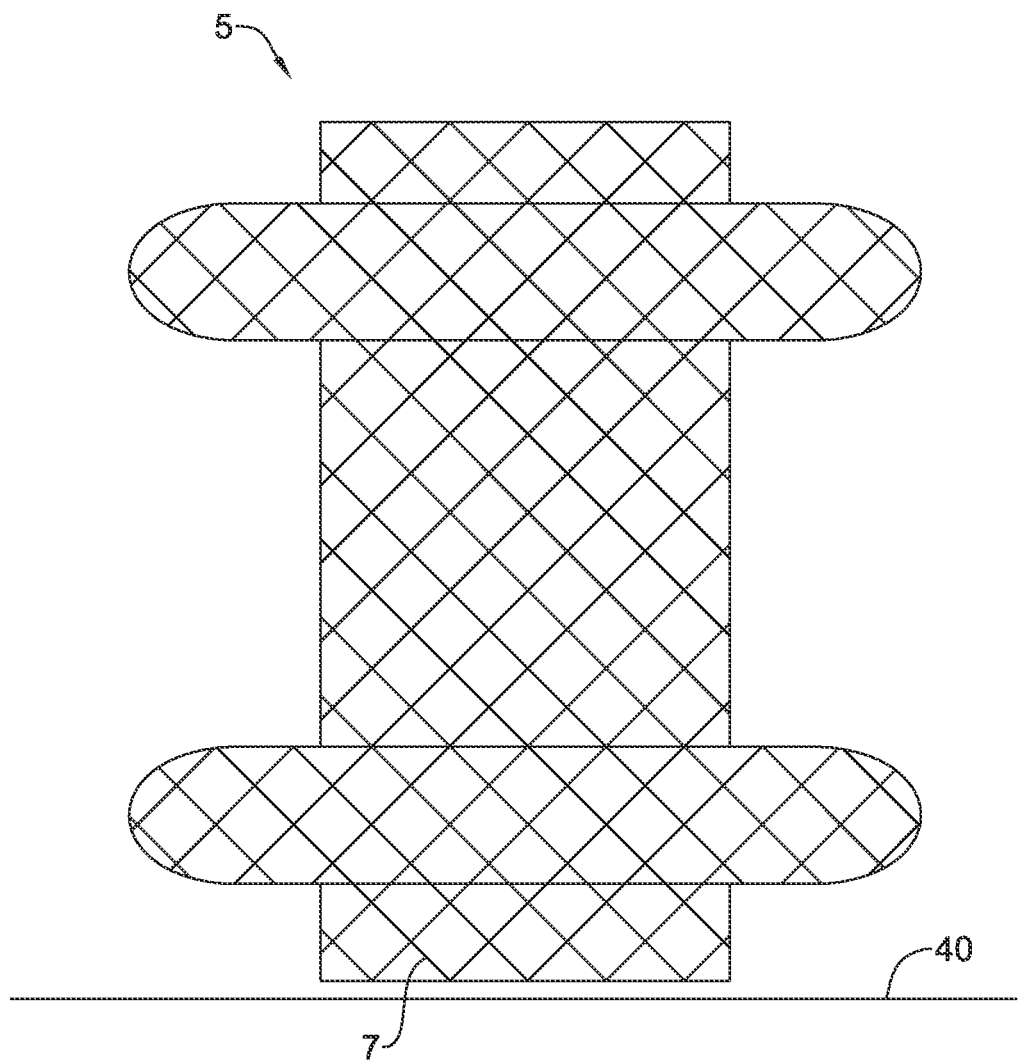
FIG. 1 is a side view of a prior art stent disposed adjacent a cyst wall.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

FIG. 1 depicts a prior art woven stent 5 positioned adjacent a tissue wall such as a cyst wall 40. As the cyst volume reduces due to drainage through the stent lumen, the terminal end 7 of the stent 5 may come in contact with the cyst wall 40, and may result in tissue irritation with resultant bleeding and/or vessel infection. Additionally the premature contact of the device end and tissue wall may leave residual pockets of cystic fluid unable to effectively drain due to the device lumen being blocked off.

Figure 2:
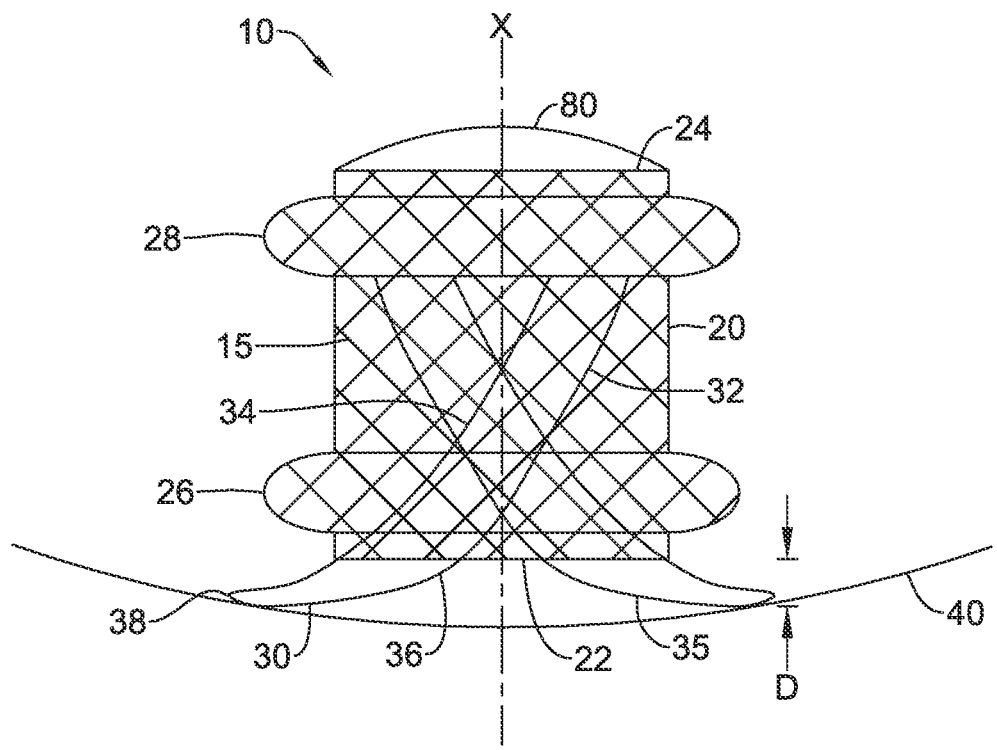
FIG. 2 is a side view of a hollow, tubular stent in accordance with an embodiment of the disclosure, adjacent a cyst wall.

FIG. 2 shows a stent 10 including a tubular body 20 and multiple atraumatic spacer members 30 extending beyond the end of the tubular body 20. The tubular body 20 is a hollow tubular structure having an open first end 22, an open second end 24, and a lumen extending therebetween. The tubular body 20 may be formed from one or more, or a plurality of wires 15. The wires 15 may be woven, braided, wound, knitted, and combinations thereof, to form the tubular body 20.

The stent 10 may include multiple wires 15 of a metal material, such as nitinol or nitinol-containing material, or other nickel-titanium alloy, for example. In some instances, the wires 15 may have a diameter of about 0.011 inches, for example. The number of wires 15 and the diameters of the wires 15, which may be the same or different, depicted in FIG. 2 are not limiting, and other numbers of wires 15 and other wire diameters may suitably be used. Desirably, an even number of wires 15 may be used, for example, from about 10 to about 36 wires 15.

Desirably, the wires 15 are made from any suitable implantable material, including without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly (phosphate ester) and the like. Wires made from polymeric materials may also include radiopaque materials, such as metallic-based powders, particulates or pastes which may be incorporated into the polymeric material. For example the radiopaque material may be blended with the polymer composition from which the polymeric wire is formed, and subsequently fashioned into the stent 10 as described herein. Alternatively, the radiopaque material may be applied to the surface of the metal or polymer wire 15 of the stent 10. In either embodiment, various radiopaque materials and their salts and derivatives may be used including, without limitation, bismuth, barium and its salts such as barium sulphate, tantalum, tungsten, gold, platinum and titanium, to name a few. Additional useful radiopaque materials may be found in U.S. Pat. No. 6,626,936, the contents of which are incorporated herein by reference. Metallic complexes useful as radiopaque materials are also contemplated. The stent may be selectively made radiopaque at desired areas along the wire or may be fully radiopaque.

In some instances, the wires 15 may have a composite construction having an inner core of tantalum, gold, platinum, tungsten, iridium or combination thereof and an outer member or layer of nitinol to provide a composite wire for improved radiopacity or visibility. In one example, the inner core may be platinum and the outer layer may be nitinol. The inner core of platinum may represent about at least 10% of the wire 15 based on the overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Pat. No. 7,101,392, the contents of which is incorporated herein by reference. The wires 15 may be made from nitinol, or a composite wire having a central core of platinum and an outer layer of nitinol. Further, the filling weld material, if required by welding processes such as MIG, may also be made from nitinol, stainless steel, cobalt-based alloy such as Elgiloy, platinum, gold, titanium, tantalum, niobium, and combinations thereof.

The tubular body 20 may have one or more anchor members 26, 28 adjacent the first and second ends, respectively. The anchor members 26, 28 may be regions that extend radially outward from the tubular body 20, forming flanges. In the example shown in FIG. 2, the anchor members 26, 28 extend circumferentially and radially outward from the tubular body 20, substantially perpendicular to the longitudinal axis X of the stent 10. The anchor members 26, 28 may have an outer diameter larger than the outer diameter of the stent body portion disposed between the anchor members 26, 28.

The stent 10 may include a plurality of atraumatic spacer members 30 disposed around the first end 22 of the tubular body, as shown in FIG. 2. In other examples, a plurality of spacer members 30 may be disposed around both the first end 22 and the second end 24. The spacer members 30 are configured to hold the first end 22 of the stent away from the cyst wall 40 as the cyst is drained and the cyst wall 40 advances toward the first end 22. The spacer members 30 prevent the cyst wall 40 of the cyst from contacting the first end 22 of the tubular body 20 of the stent 10. Even when the cyst has fully drained, the spacer members 30 may prevent contact between the cyst wall and the first end 22 of the tubular body 20, thus preventing damage to the tissue wall by contacting the bare first end 22 of the stent. In some instances, the spacer members 30 may be formed from the wires 15 defining the tubular body 20. For example, the spacer members 30 may be formed by extending one or more wires 15 from the first end 22 of the tubular body 20 and then weaving that wire back into the tubular body 20. In other examples, the spacer members 30 may be formed from additional wires added to a previously formed tubular body 20. The spacer members 30 may have a first region 36 disposed adjacent the first end 22 of the tubular body 20, and a terminal end 38 which is the point of the spacer member 30 furthest away from the first end 22 of the tubular body 20 measured along the length of the spacer member 30. The spacer members 30 may be formed from a biocompatible material such as the metallic and polymeric materials listed above for the wires 15 of the tubular body 20. The spacer members 30 may be self-supporting, such that the spacer members 30 may be cantilevered and/or extend from the first end 22 of the tubular body 20 while retaining their shape. However, when the spacer members 30 engage a lumen wall, the spacer members 30 may provide insufficient radial resistance to anchor the stent 10.

In the example shown in FIG. 2, the spacer members 30 are each formed from a single wire 35 formed in a loop and attached to the previously formed tubular body 20, with ends of the wire loop defining legs 32, 34 attached to an inner surface of the tubular body 20. In other examples, multiple spacer members 30 may be formed from a single wire. The legs 32, 34 may be welded onto the inside of the tubular body 20. Alternatively, the legs 32, 34 may be attached with adhesive, wire wrapping, or other suitable permanent connection. In some instances, the legs 32, 34 may be woven into the wires 15 of the tubular body 20. The legs 32, 34 may extend over 25% or more, 50% or more, or 75% or more of the length of the tubular body 20, from the first end 22 toward the second end 24. In some examples, the legs 32, 34 extend over the entire length of the tubular body 20 from the first end 22 to the second end 24. The legs 32, 34 may extend along the inner surface of the tubular body 20 substantially parallel to the longitudinal axis or at an oblique angle to the longitudinal axis, and thus in a helical direction. In some examples, the legs 32, 34 may follow the path of and be juxtaposed along the wires 15 in the braiding pattern of the stent 10.

The legs 32, 34 from one spacer member 30 may overlap the legs 32, 34 of another spacer member 30 in some instances. For example, in some embodiments, the legs 32, 34 of a first spacer member 30 may extend in a first helical direction along the inner surface of the tubular body 20 while the legs 32, 34 of a second spacer member 30 may extend in an opposite second helical direction along the inner surface of the tubular body 20 and intersect the legs 32, 34 of the first spacer member 30. In other examples, all of the legs 32, 34 of all spacer members 30 extend along the interior of the tubular body 20 without contacting legs 32, 34 of another spacer member 30. For example, the legs 32, 34 of each spacer member 30 may extend in the same helical direction along the interior of the tubular body 20.

Figure 3:
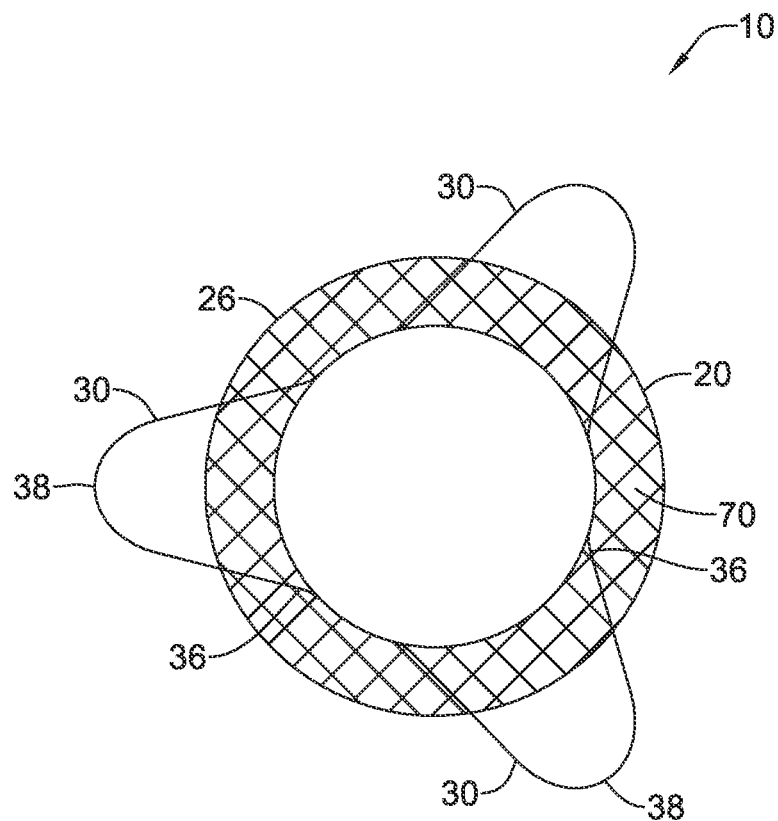
FIG. 3 is an end view of the stent of FIG. 2.

The spacer members 30 may be arranged uniformly around the circumference of the first end 22 and radiate outward in a radial direction. The spacer members 30 may be spaced apart, as shown in FIG. 3. In other examples, spacer members 30 may overlap with an adjacent spacer member 30 around the circumference of the first end 22. For instance, each spacer member 30 may overlap with the adjacent spacer member 30 on each side thereof. As depicted in FIG. 3 the stent 10 includes three spacer members 30. In other embodiments, the stent 10 may have two opposing spacer members 30, or four, five, six, or more spacer members 30 evenly or unevenly spaced around the circumference of the stent 10.

The wire 35 forming the spacer members 30 may have the same or different properties than the wires 15 which form the tubular body 20. For example, the wires 35 may be of the same or different stiffness or flexibility, all of which may be tailored for a particular application. In some embodiments, the wire 35 forming spacer members 30 may be stiffer than the stent wires 15 forming the tubular body 20 of the stent 10. In some instances, the wire 35 forming the spacer members 30 may be formed of a different material and/or may have a different diameter than the stent wires 15. In some instances, the wire 35 forming the spacer members 30 may be stainless steel while the stent wires 15 may be formed of a nickel-titanium alloy, such as nitinol. The material forming the spacer member wires 35 may have a stiffness greater than, equal to, or less than the material forming the wires 15 of the tubular body 20 and/or the material forming the spacer member wires 35 may have a modulus of elasticity (Young's modulus) greater than, equal to, or less than the material forming the wires 15 of the tubular body 20. The choice of material, wire diameter and pre-treatment of the wires 35, 15 and stent configuration are some of the factors which may be varied to achieve particular stent properties. Additionally, at least one of the spacer members 30 may also be made radiopaque by various methods, for example with a coating or finish, with a band or as part of the stent material. Color or different finishes may also be added to the spacer members 30 to visually differentiate them from the rest of the stent wires 15.

The spacer members 30 are configured such that applying a pulling or squeezing force on the spacer members 30 does not reduce the outer diameter of the tubular body 20. In examples in which spacer members 30 are formed from additional wires attached to the previously formed tubular body 20, the attachment is such that pulling on the spacer members 30 does not reduce the outer diameter of the tubular body 20. For example, welding the spacer members 30 or using adhesive to attach the spacer members 30 to one or more wire cross-over points on the inner surface of the tubular body 20 may prevent the spacer members 30 from interacting with the weave or braided structure of the tubular body 20 to reduce its diameter when the spacer members 30 are pulled or squeezed. In examples where the spacer members 30 are formed from one or more wires used in forming the tubular body 20, the portion of the wire(s) forming the spacer members 30 may be stabilized relative to the tubular body 20 such that pulling on the spacer members 30 does not reduce the outer diameter of the tubular body 20. In one example, stabilizing may include welding one or more of the last wire cross-over points at the first end 22 of the tubular body where the wire forming the spacer member 30 exits the tubular body 20. In other examples, adhesive or additional wire wrapping may be used to stabilize the spacer members 30 relative to the tubular body 20. The spacer members 30 thus do not function as retrieval elements to reduce the diameter of the stent 10 for removal. In some examples, a separate retrieval element 80 may be disposed on the second end 24 and/or the first end 22 of the tubular body 20. In the example shown in FIG. 2, the stent 10 includes a retrieval element 80 attached to the second end 24 of the tubular body 20. In some instances, the retrieval element 80 may be a wire or suture woven through loops of the wires 15 of the tubular body 20 at the second end 24 of the tubular body 20.

The spacer members 30 extend longitudinally beyond the first end 22 of the tubular body 20. The spacer members 30 may extend beyond the first end 22 of the tubular body 20 for a distance D. In some instances, distance D may be 5% to 50%, 10% to 50%, 10% to 30%, or 5% to 30% of the total length of the tubular body 20, for example. In some examples, the spacer members 30 may extend 8 mm to 15 mm beyond the first end 22. The spacer members 30 may also extend radially away from the tubular body 20, beyond the outer diameter of the tubular body 20 as measured at the first end 22. In the example shown in FIGS. 2 and 3, the spacer members 30 also extend radially beyond the outer diameter of the anchor members 26, 28. For example, the spacer members 30 may extend radially outward at an angle of between about 20 degrees to about 85 degrees, between about 25 degrees to about 75 degrees, about 30 degrees to about 60 degrees, or about 45 degrees to about 75 degrees from the longitudinal axis X of the stent 10. The angle of the spacer members 30 relative to the longitudinal axis X may be, for example, 25 degrees or more, 30 degrees or more, 35 degrees or more, 40 degrees or more, 45 degrees or more, 50 degrees or more, 55 degrees or more, 60 degrees or more, 65 degrees or more, 70 degrees or more, 75 degrees or more, 80 degrees or more, or 85 degrees or more degrees, or other desired angle. The spacer members 30 illustrated in the figures are shaped as elongated loops. In other examples, the spacer members 30 may be any shape desired, including circular, elliptical, teardrop, etc. The terminal end 38 of the spacer members 30 may be rounded, as shown in FIG. 3, to provide an atraumatic end that engages the cyst wall 40.

Figure 4:
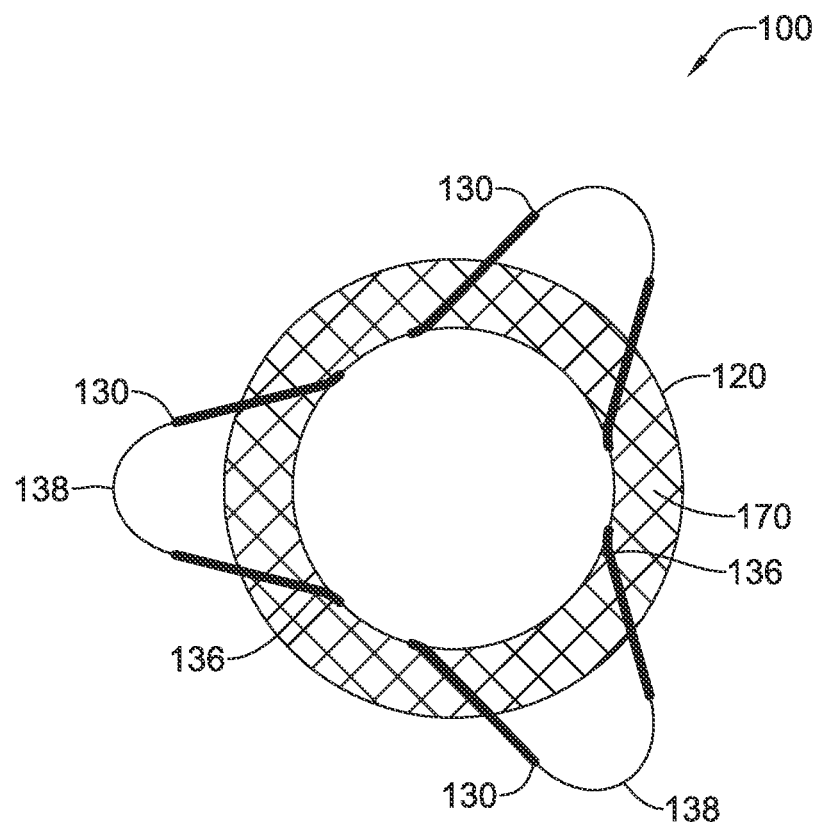
FIG. 4 is an end view of a stent in accordance with another embodiment of the disclosure.

The spacer members 30 may provide a structure which has the required stiffness to maintain the stent 10 in a spaced orientation away from the cyst wall 40, thus preventing damage to the tissue wall from contact with the first end 22 of the tubular body 20. In some examples, the flexibility of the spacer members 30 varies along their length. The spacer members 30 may be formed from a wire having a variable thickness along its length. In one example, as shown in FIG. 4, the stent 100 includes at least one spacer member 130 formed from a wire having a first thickness in the first region 136 adjacent the tubular body 120, tapering down and/or transitioning to a second thickness at the terminal end 138. As illustrated in FIG. 4, the second thickness may be smaller than the first thickness to achieve a spacer member 130 that is more flexible at the terminal end 138. The more flexible terminal end 138 may allow the spacer member 130 to bend slightly at the terminal end 138 as it contacts the cyst wall 40, reducing the potential for tissue injury.

In some embodiments the stent 10, 100 may include a covering 70, 170 disposed over at least a portion of the tubular body 20, 120 of the stent 10, 100. For example, the covering 70, 170 may fully cover the entire length of the tubular body 20, 120 of the stent 10, 100, forming a fully covered stent in which all of the interstices defined in the braided or woven pattern are covered with the covering 70, 170 to prevent tissue in-growth and fluid leakage into the lumen of the tubular body 20, 120. In other examples, the covering 70, 170 may cover only a portion of the length of the tubular body 20, 120 of the stent 10, 100, forming a partially covered stent in which a portion of the interstices defined in the braided or woven pattern remain uncovered, allowing tissue in-growth. In some instances, the spacer members 30, 130 may be covered by the covering 70, 170, thus the entire stent 10, 100, including both the entire tubular body 20, 120 and the spacer members 30, 130 may be covered by the covering 70, 170. For instance, the covering 70, 170 may extend across and fill the space between adjacent sides of the loop formed by the wire(s) forming the spacer members 30, 130 while the gap between adjacent spacer members 30, 130 may be devoid of any covering material, permitting fluid to flow between the spacer members 30, 130 around the end of the stent 10, 100 and into the lumen of the stent 10, 100. In some instances, the stent 10, 100 may be dipped into a solution of silicone or other polymer to form the covering 70, 170. In other instances, a polymer sheet or tube may be placed around the tubular body 20, 120 and/or within the tubular body 20, 120 to form the covering 70, 170. The covering 70, 170 may be disposed on external or internal surfaces of the tubular body 20, 120, or on both the internal and external surfaces of the tubular body 20, 120, thereby embedding the stent 10, 100 in the polymeric material. The coating or covering may be a polymer covering, such as a polytetrafluoroethylene (PTFE) or silicone covering, however other coverings, particularly elastomeric polymers, may be used. Non-limiting examples of useful polymeric materials include polyesters, polypropylenes, polyethylenes, polyurethanes, polynaphthalenes, polytetrafluoroethylenes, expanded polytetrafluoroethylene, silicone, and combinations and copolymers thereof.

Figure 5:
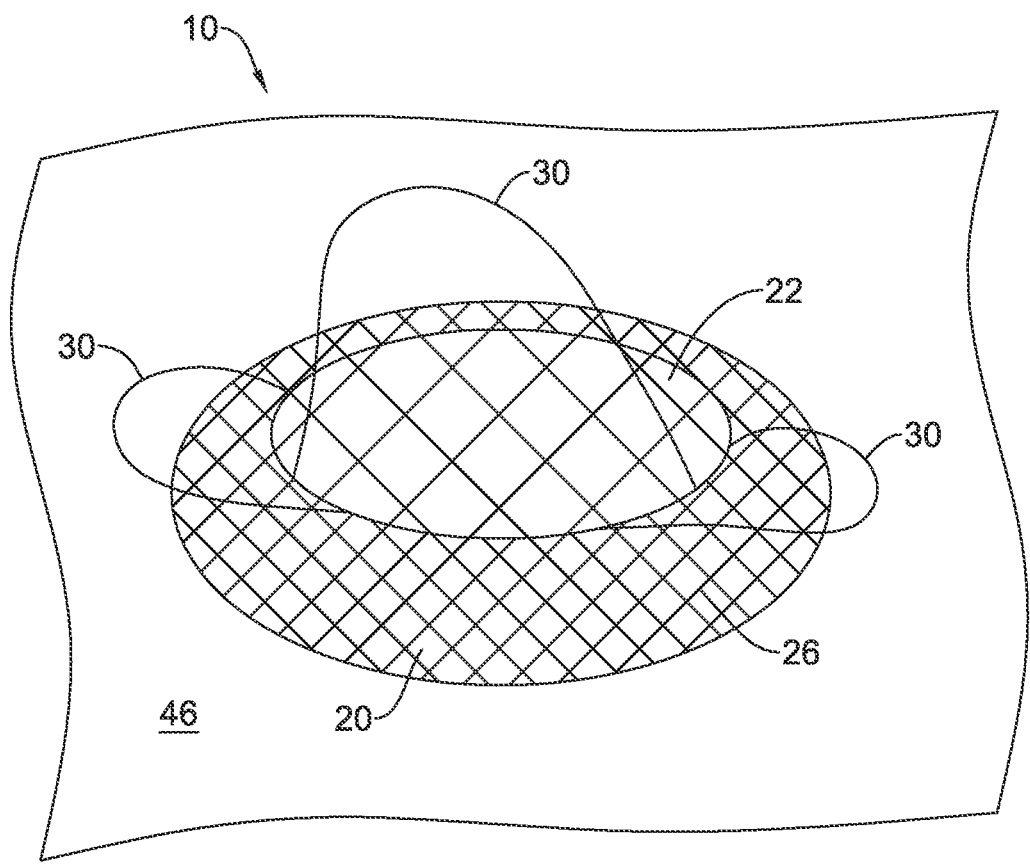
FIG. 5 is a perspective view of the end of the stent of FIG. 2 positioned in a tissue structure.

FIG. 5 shows one end of the stent 10 of FIG. 2 implanted in a tissue site represented as a cyst. In a method of draining a cyst, the first end portion of the stent 10 may be implanted through an opening in a tissue wall with the first anchor member 26, first end 22 of the tubular body 20, and three spacer members 30 all protruding through the tissue wall 46 into a cavity representing the cyst. The second anchor member 28 may be disposed on the other side of the tissue wall to secure the stent 10 across the tissue wall 46. The larger diameter of the first anchor member 26 holds the stent 10 in place and the spacer members 30 are disposed within the cyst. As the cyst volume decreases due to drainage through the lumen of the stent 10, the lower cyst wall (see FIG. 2) will contact the spacer members 30, instead of the first end 22 of tubular body 20. The spacer members 30 prevent the wall of the cyst from contacting the first end 22 of the tubular body 20. The spacer members 30 hold the first end 22 of the tubular body 20 away from the cyst wall and permit fluid to pass around the first end 22 of the tubular body 20 between adjacent spacer member 30 and into the lumen of the tubular body 20 to drain the fluid from the cyst. Even when all fluid has been drained from the cyst, the cyst wall is spaced away from the first end 22 of the tubular body 20 by the spacer members 30. This spacing may reduce or eliminate tissue irritation and/or resultant bleeding.

Figure 6A:
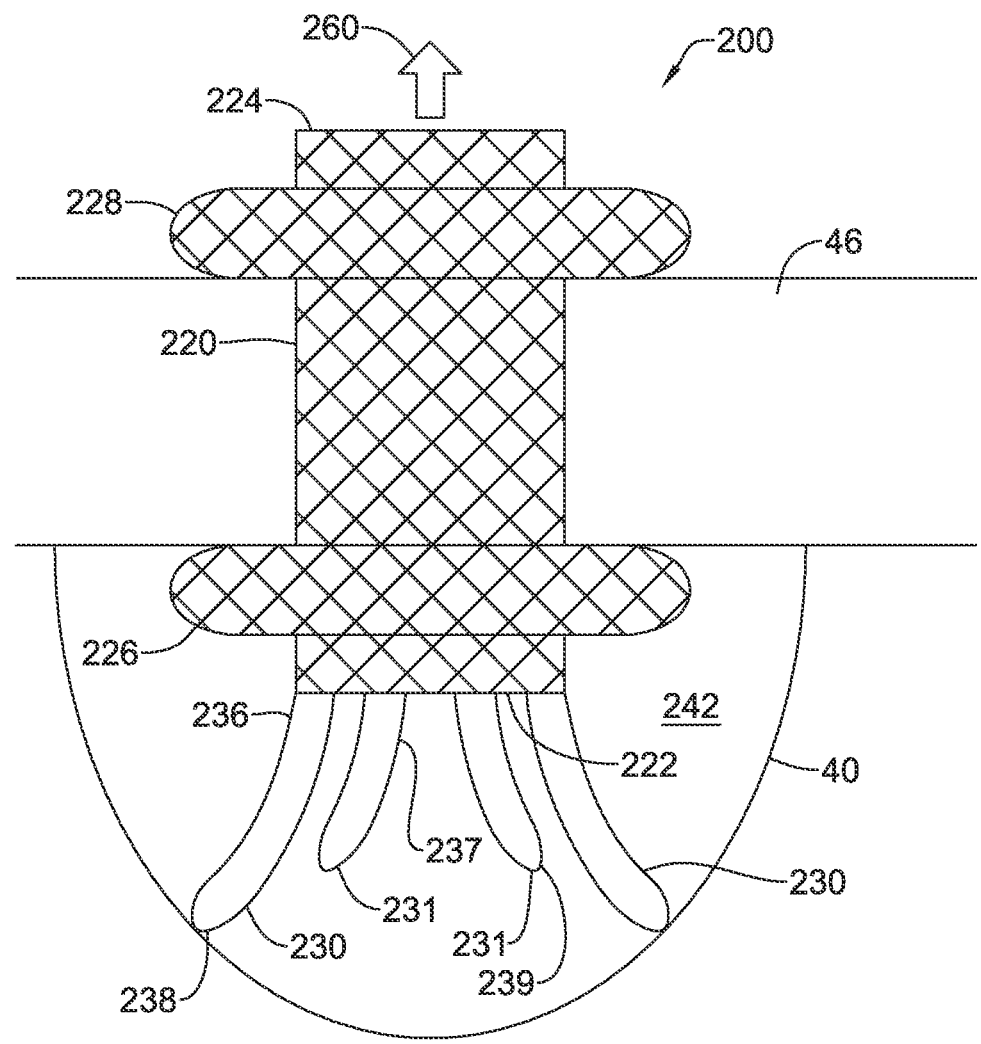
FIGS. 6A and 6B are side partial cross-sectional views of a stent in accordance with another embodiment of the disclosure implanted in a target tissue structure.
Figure 6B:
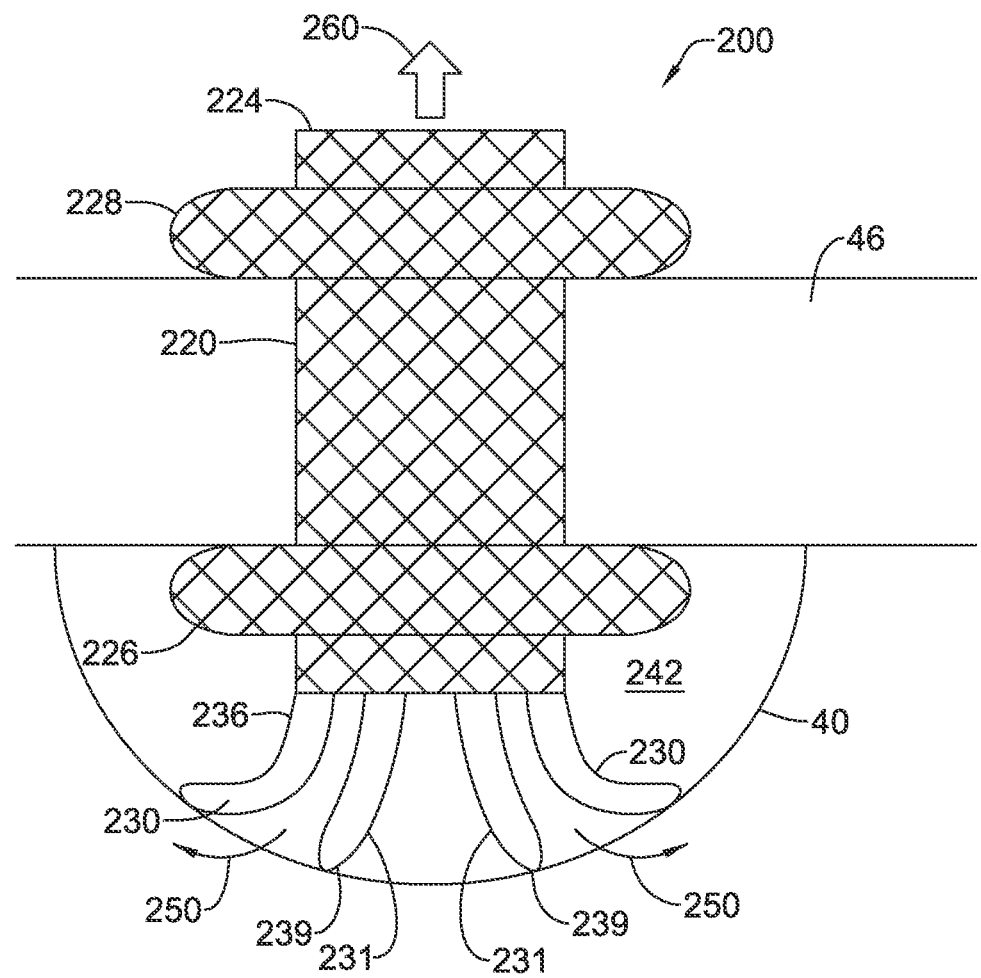

FIGS. 6A and 6B illustrate another example of a stent 200 disposed through a tissue wall 46 with the first end 222 of the stent 200 disposed in the cavity of a cyst 242. The stent 200 includes a tubular body 220, a first group of spacer members 230 having a first length extending from the first region 236 adjacent the first end 222 of the tubular body 220 to the terminal end 238 of spacer members 230. The stent 200 includes a second group of spacer members 231 extending from the first region 237 adjacent the first end 222 of the tubular body 220 to the terminal end 239 of spacer members 231. The second group of spacer members 231 have a second length that is shorter than the first length of the first group of spacer members 230, positioning the terminal ends 239 of the second group of spacer members 231 closer to the first end 222 of the tubular body 220 than the terminal ends 238 of the first group of spacer members 230. As the fluid in the cyst 242 is drained through the lumen of the stent 200, in direction of arrow 260, the cyst wall 40 collapses and engages the terminal ends 238 of the first group of spacer members 230, as shown in FIG. 6A. Then, as the cyst continues to drain and the cyst wall 40 advances toward the first end 222 of the tubular body 220, the first group of spacer members 230 may flex or bend back toward the second end 224 of the tubular body 220, in the direction of arrow 250, permitting the terminal ends 239 of the second group of spacer members 231 to engage the cyst wall 40, as shown in FIG. 6B.

The first group of spacer members 230 may be more flexible than the second group of spacer members 231, allowing the first group of spacer members 230 to flex, bend or partially collapse as the cyst wall 40 advances towards the first end 222 of the tubular body 220. As with the spacer members 30 described above, the first and second groups of spacer members 230, 231 may have a variable flexibility along their length. In particular, one or both of the first and second groups of spacer members 230, 231 may have terminal ends 238 that are more flexible than first regions 236 adjacent the tubular body 320. As with the stent 10 described above, when the first and second groups of spacer members 230, 231 engage a lumen wall, the spacer members 230, 231 provide insufficient radial resistance to anchor the stent 200. Similar to the spacer members 30 discussed above, the spacer members 230, 231 are configured such that applying a pulling or squeezing force on the spacer members 230, 231 does not reduce the outer diameter of the tubular body 220.

Figure 7:
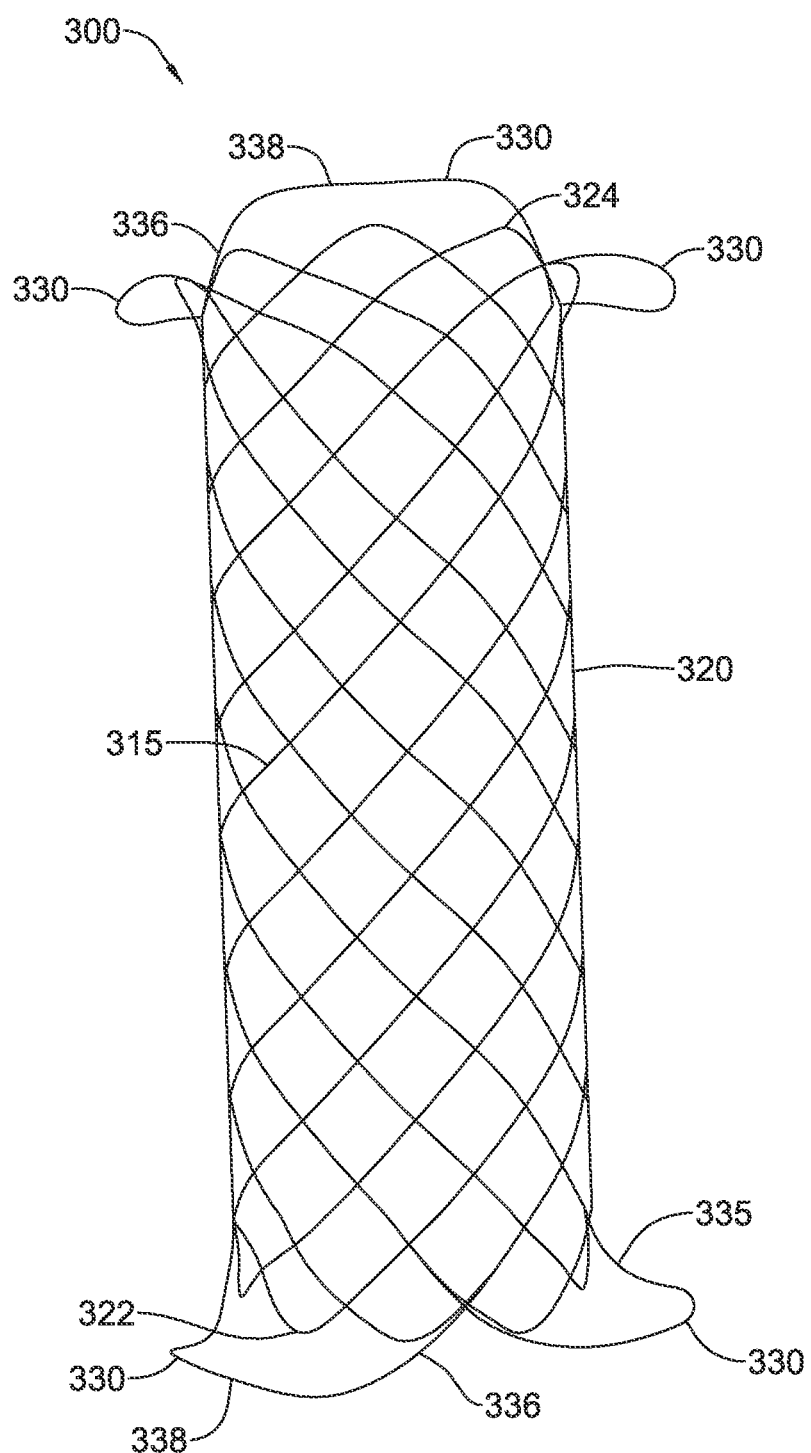
FIG. 7 is a side view of a stent in accordance with a further embodiment of the disclosure.

A further example of a stent 300 with a tubular body 320 and a plurality of spacer members 330 is shown in FIG. 7. In this example, the tubular body 320 is formed from one or more stent wires 315 and has a substantially uniform diameter along its length, without anchor members. The plurality of spacer members 330 may be attached to the first end 322 of the tubular body 320, the second end 324 of the tubular body 320, or both. The spacer members 330 may be formed from wires 315 forming the tubular body 320, or from wires 335 attached to the tubular body 320 after the tubular body 320 has been formed. As with the stent 10 discussed above, the wires 335 may be attached to the tubular body 320 by welding, adhesive, wire wrapping or other suitable permanent connection. Also as with the stent 10 discussed above, the spacer members 330 are configured such that applying a pulling or squeezing force on the spacer members 330 does not reduce the outer diameter of the tubular body 320.

Figure 8:
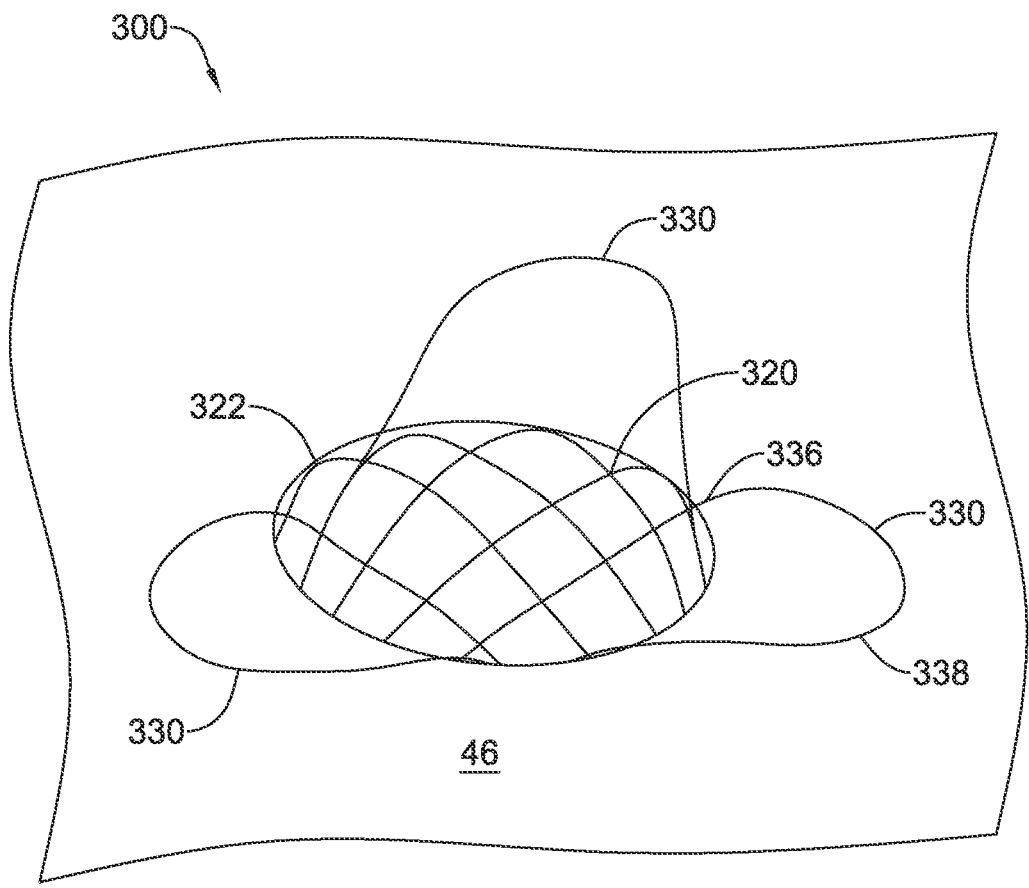
FIG. 8 is a perspective view of the end of the stent of FIG. 7 in a tissue structure.

The wires 335 may be tapered to provide a variable flexibility along the spacer member 330. For example, the wires 335 may have a first thickness in the first region 336 adjacent the tubular body 320 and taper down to a second, smaller thickness in the region of the terminal end 338 of the spacer member 330, resulting in the terminal end 338 being more flexible than the first region 336. This allows the terminal end 338 of the spacer members 330 to flex or bend back toward the opposite end of the tubular body 320 upon contact with a tissue wall. The stiffer first region 336 holds the end of the tubular body 320 away from the tissue wall allowing fluid drainage around the first end 322 of the tubular body 320 into the lumen of the stent 300. The flexibility of the terminal end 338 of the spacer members 330 allows the spacer members 330 to gently engage the tissue wall below the stent 300, but the spacer members 330 provide insufficient radial resistance to anchor the stent 300 against lumen walls extending substantially parallel to the longitudinal axis. The stiffer first region 336 may provide sufficient resistance in a longitudinal direction to anchor the stent 300 disposed perpendicular to a tissue wall. FIG. 8 shows the first end 322 of the tubular body 320 extending through an opening in a tissue wall 46. In this example of the stent 300, the spacer members 330 have the dual function of holding the stent 300 in place within the opening in the tissue wall, and spacing the first end 322 of the tubular body 320 of the stent 300 from the tissue wall as the cyst drains.

Figure 9:
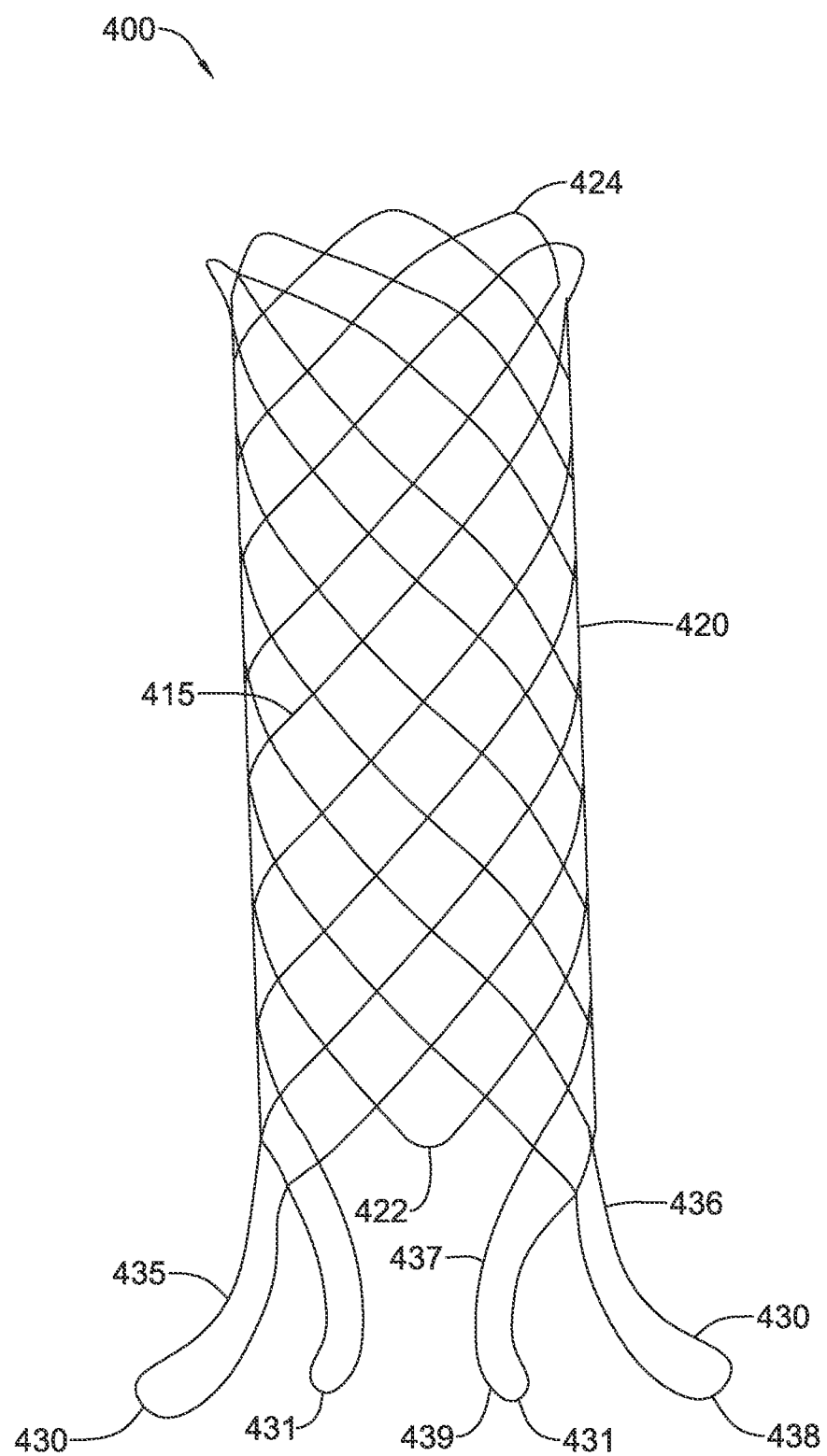
FIG. 9 is a side view of a stent in accordance with another embodiment of the disclosure.

FIG. 9 shows another example of a stent 400 with a tubular body 420 formed from one or more wires 415 woven, braided, knitted, or wound into the tubular body 420. The stent 400 includes a first group of spacer members 430 having a first length extending from the first region 436 adjacent the first end 422 of the tubular body 420 to the terminal end 438 of the spacer members 430. The stent 400 includes a second group of spacer members 431 extending from the first region 437 adjacent the first end 422 of the tubular body 420 to the terminal end 439 of the spacer members 431. The second group of spacer members 431 have a second length that is shorter than the first length of the first group of spacer members 430, positioning the terminal ends 439 of the second group of spacer members 431 closer to the first end 422 of the tubular body 420 than the terminal ends 438 of the first group of spacer members 430. The first group of spacer members 430 may be more flexible than the second group of spacer members 431, allowing the first group of spacer members 430 to flex, bend or partially collapse as the cyst drains and the tissue wall advances towards the first end 422 of the tubular body 420. In this example, the tubular body 420 has a substantially uniform diameter along its length, without anchor members. The first and second groups of spacer members 430, 431 may be attached to the first end 422 of the tubular body 420, the second end 424 of the tubular body 420, or both. The spacer members 430, 431 may be formed from wires 415 forming the tubular body 420 or wires 435 attached to the tubular body 420 after the tubular body 420 has been formed. As with the stent 10 discussed above, the spacer members 430, 431 are configured such that applying a pulling or squeezing force on the spacer members 430, 431 does not reduce the outer diameter of the tubular body 420. The wires 435 may be tapered to provide a variable flexibility along the spacer members 430, 431. For example, the wires 435 may have a first thickness in the first region 436, 437 adjacent the tubular body 420 and taper down or transition to a second, smaller thickness in the region of the terminal end 438, 439, resulting in the terminal end 438, 439 being more flexible than the first region 436, 437. This allows the terminal end 438, 439 of the spacer members 430, 431 to bend back toward the second end 424 of the tubular body 420 upon contact with a tissue wall. The stiffer first region 436, 437 holds the end of the tubular body 420 away from the tissue wall. The flexibility of the terminal end 438, 439 of the spacer members 430, 431 allows the spacer members 430, 431 to gently engage the tissue wall below the stent 400, but provide insufficient radial resistance to anchor the stent 400 against lumen walls extending substantially parallel to the longitudinal axis. The stiffer first region 436, 437 may provide sufficient resistance in a longitudinal direction to anchor the stent 400 disposed perpendicular to a tissue wall.

As with the stent 10, stents 100, 200, 300 and 400 may include a covering, similar to covering 70, 170 described above, disposed over at least a portion of the tubular body of the stent 100, 200, 300, 400. For example, the covering may fully cover the entire length of the tubular body of the stent 100, 200, 300, 400, forming a fully covered stent in which all of the interstices defined in the braided or woven pattern are covered with the covering to prevent tissue in-growth and fluid leakage into the lumen of the tubular body. In other examples, the covering may cover only a portion of the length of the tubular body of the stent 100, 200, 300, 400, forming a partially covered stent in which a portion of the interstices defined in the braided or woven pattern remain uncovered, allowing tissue in-growth. In some instances, the spacer members 130, 230, 330, 430 may be covered by the covering, thus the entire stent 100, 200, 300, 400, including both the entire tubular body and the spacer members 130, 230, 330, 430 may be covered by the covering. For instance, the covering may extend across and fill the space between adjacent sides of the loop formed by the wire(s) forming the spacer members 130, 230, 330, 430, while the gap between adjacent spacer members 130, 230, 330, 430 may be devoid of any covering material, permitting fluid to flow between the spacer members 130, 230, 330, 430 around the end of the stent 100, 200, 300, 400 and into the lumen of the stent 100, 200, 300, 400.

Various stent types and stent constructions may be employed for the stent 10, 100, 200, 300, 400. For example, the stent 10, 100, 200, 300, 400 may be a self-expanding stent or a balloon expandable stent. The stent 10, 100, 200, 300, 400 may be capable of radially contracting to a compressed or collapsed configuration for delivery, and then expandable to an expanded configuration during deployment in the body lumen. Thus, the stent 10, 100, 200, 300, 400 may be described as radially distensible or deformable. Self-expanding stents include those that have a spring-like action which causes the stent to radially expand, or stents which expand due to the memory properties of the stent material for a particular configuration at a certain temperature. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. In other embodiments, the stent 10, 100, 200, 300, 400 may be formed as a monolithic tubular member by etching or cutting a pattern of interconnected struts from a tube.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

The invention claimed is:

1. A stent comprising:
   a tubular body formed of one or more interwoven wires, the tubular body defining a lumen and having first and second opposing open ends and a length extending therebetween, the tubular body having an outer diameter; and a plurality of spacer members disposed around only the first open end and extending longitudinally away from and beyond the first open end of the tubular body, the plurality of spacer members each formed of a single wire forming an elongated loop extending radially outward beyond an outermost extent of the outer diameter of the tubular body, wherein when a pulling or squeezing force is applied to the plurality of spacer members, the outer diameter of the tubular body is not reduced;

wherein each wire forming the elongated loop of one of the plurality of spacer members is separate from the one or more interwoven wires forming the tubular body and fixed to the tubular body;

wherein each wire forming the elongated loop of one of the plurality of spacer members is less flexible than the one or more interwoven wires forming the tubular body.

2. The stent of claim 1, wherein each of the plurality of spacer members has a base region coupled to the tubular body and an opposing free end region, wherein the free end region is more flexible than the base region.

3. The stent of claim 2, wherein each wire forming one of the elongated loops has a first thickness in the base region and a second thickness in the free end region, wherein the second thickness is smaller than the first thickness.

4. The stent of claim 1, wherein the plurality of spacer members includes a first group having a first length and a second group having a second length, where the first length is longer than the second length.

5. The stent of claim 4, wherein the first group is more flexible than the second group.

6. The stent of claim 1, further comprising a first anchor member extending circumferentially around the tubular body adjacent the first open end, and a second anchor member extending circumferentially around the tubular body adjacent the second open end, the first and second anchor members each extending radially outward from the tubular body and each having an outer diameter larger than the outer diameter of the tubular body, the first and second anchor members each being formed from the one or more interwoven wires forming the tubular body.

7. The stent of claim 6, wherein a portion of the tubular body extends beyond the first anchor member away from the second open end and defines the first open end.

8. The stent of claim 6, further comprising a retrieval element disposed at the second open end.

9. The stent of claim 6, wherein each wire forming the elongated loop of one of the plurality of spacer members has first and second legs fixed to a portion of the tubular body and extending along the tubular body toward the second open end.

10. The stent of claim 9, wherein the first and second legs extend along over 25% or more of the length of the tubular body.

11. The stent of claim 1, further comprising a covering extending over an entirety of the tubular body and the plurality of spacer members.

12. A stent comprising:
a tubular body formed from one or more interwoven wires, the tubular body defining a lumen and having first and second opposing open ends and a length extending therebetween, the tubular body having an outer diameter;

a first anchor member extending circumferentially around the tubular body adjacent the first open end, and a second anchor member extending circumferentially around the tubular body adjacent the second open end, the first and second anchor members each extending radially outward from the tubular body and each having an outer diameter larger than the outer diameter of the tubular body, the first and second anchor members each being formed from the one or more interwoven wires forming the tubular body; and a plurality of spacer members disposed around only the first open end and extending longitudinally away from and beyond the first open end of the tubular body, the plurality of spacer members extending radially outward beyond the outer diameter of the tubular body and the outer diameter of the first anchor member, wherein each of the plurality of spacer members is formed from a single wire forming an elongated loop that has a base region having first and second legs of the single wire each fixed to the tubular body at spaced apart locations and an opposing free end region forming an apex of the elongated loop, wherein when a pulling or squeezing force is applied to the plurality of spacer members, the outer diameter of the tubular body is not reduced.

13. The stent of claim 12, wherein each wire forming the elongated loop of one of the plurality of spacer members is separate from the one or more interwoven wires forming the tubular body, wherein the wires forming the elongated loops of the plurality of spacer members are fixed to an interior surface of the tubular body.

14. The stent of claim 13, wherein the first and second legs of each elongated loop extends along the tubular body and extending toward the second open end.

15. The stent of claim 12, wherein a portion of the tubular body extends beyond the first anchor member away from the second open end and defines the first open end.

16. A stent comprising:
a tubular body formed of one or more interwoven wires, the tubular body having first and second opposing open ends and a lumen extending therebetween;

a first anchor member disposed adjacent the first open end and a second anchor member disposed adjacent the second open end, the first and second anchor members each being formed from the one or more interwoven wires forming the tubular body and extending radially outward from the tubular body beyond an outer diameter of the tubular body; and a plurality of spacer members disposed around only the first open end and extending longitudinally away from and beyond the first open end, wherein the plurality of spacer members are formed from one or more wires of the one or more interwoven wires forming the tubular body, wherein a portion of one or more interwoven wires forming the plurality of spacer members are stabilized relative to the tubular body by welding one or more cross-over points at the first open end of the tubular body where wire forming the spacer members exits the tubular body.

17. The stent of claim 1, wherein each elongated loop that has a base region having first and second legs of the single wire each fixed to the tubular body at spaced apart locations and an opposing free end region forming an apex of the elongated loop.

* * * * *